United States Patent [19]

Leu et al.

[11] Patent Number: 5,108,191

[45] Date of Patent: Apr. 28, 1992

[54] METHOD AND APPARATUS FOR DETERMINING CURIE TEMPERATURES OF FERROMAGNETIC MATERIALS

[75] Inventors: Ming-Sheng Leu, Taipei; Chorng-Sheng Tsai, Hsinchu; Ming-Jhy Jiang, Taipei; Yng-Jye Yu; Chun-Sien Lin, both of Hsinchu, all of Taiwan

[73] Assignee: Industrial Technology Research Institute, Taiwan

[21] Appl. No.: 581,044

[22] Filed: Sep. 12, 1990

[51] Int. Cl.⁵ .................. G01N 25/20; G01K 7/00; G01K 7/36
[52] U.S. Cl. ......................... 374/10; 374/16; 374/11; 374/176
[58] Field of Search ............ 374/10, 11, 12, 13, 374/16, 176, 177

[56] References Cited

U.S. PATENT DOCUMENTS

| | | | |
|---|---|---|---|
| 3,283,560 | 11/1966 | Harden et al. | 374/11 |
| 3,568,050 | 3/1971 | Dill | 374/176 |
| 3,646,813 | 3/1972 | Kuznietz et al. | 374/176 |
| 4,371,272 | 2/1983 | Iwasaki | 374/184 |
| 4,596,150 | 6/1986 | Kuhr | 374/176 |
| 4,681,729 | 7/1987 | Pendleton et al. | 374/177 |
| 4,812,051 | 3/1989 | Paulik et al. | 374/10 |

FOREIGN PATENT DOCUMENTS

| | | |
|---|---|---|
| 2486661 | 1/1982 | France. |
| 0082436 | 7/1981 | Japan .................. 374/10 |
| 1318948 | 6/1987 | U.S.S.R. . |

OTHER PUBLICATIONS

Taylor et al., "Characterization of Amorphous Alloys by Thermal Analysis Techniques", Journal of Materials Science, vol. 23, pp. 2613–2621, (1988).
Greer, A. L., "The Use of DSC to Determine the Curie Temperature of Metallic Glasses", Thermochimica Acta, vol. 42, pp. 193–222, (1980).

*Primary Examiner*—William A. Cuchlinski, Jr.
*Assistant Examiner*—Diego F. F. Gutierrez
*Attorney, Agent, or Firm*—Scully, Scott, Murphy & Presser

[57] ABSTRACT

A method and the instrument associated therewith for determining the Curie points of ferromagnetic materials which display no significant abrupt change in heat absorption around the Curie points thereof by means of a conventional thermal analyzer with externally added facilities to provided an external magnetic field. The abrupt change of heat absorption of the ferromagnetic materials is increased by adding the external magnetic field to increase the magnetic anisotropy energy thereof and to strengthen the spontaneous magnetization thereof.

20 Claims, 7 Drawing Sheets

METHOD AND APPARATUS FOR DETERMINING CURIE TEMPERATURES OF FERROMAGNETIC MATERIALS

FIELD OF THE INVENTION

The present invention relates, n general, to a technique for determining the Curie points of ferromagnetic material, and, in particular, to the determination of the Curie points of materials, which do not significantly change heat absorbability around the Curie point, using a thermal analyzer having an external magnetic field applied to the material for which the Curie point is to be determined.

BACKGROUND OF THE INVENTION

According to current theory, the smallest magnetic particle is the magnetic dipole, which as the name suggests, is a combination of a positive and a negative magnetic pole. The existence of a dipole is essentially due to the spins of the electrons possessed by an atom (i.e. dipole moment). The dipole moment of atoms that constitutes a material point in random directions to reduce free energy thereof, thus, exhibits no net magnetism.

The atomic dipoles constituted by the electron spins of certain elements, such as the ferromagnetic elements, significantly point in the same direction when an external magnetic field is applied thereto. The material is said to be magnetized and this is called spontaneous magnetization. A perfect alignment of the atomic dipoles of a ferromagnetic material only exists at absolute zero. The thermal energy of finite temperature causes the dipoles to fluctuate and therefore deviate from perfect alignment. It is a process of increasing entropy. The randomizing effect gets more important when temperature gets higher and may considerably reduce the intensity of magnetization. At the Curie point, the dipoles have completely random alignment. Above the Curie point, a ferromagnetic material behaves paramagnetically. During the phase transition, the spins of an atom of a material absorb a great amount of energy and the material takes in a great amount of heat. This is the basic principle that a thermal analyzer applies to detect the Curie point of a material.

The characteristic of abrupt change of heat absorbability is the essential feature of the Curie point. By making use of this feature, commercially available thermal analyzers are constructed to detect the Curie temperature. One of them is the DSC (differential scanning calorimeter) thermal analyzer built by Du Pont Co., U.S.A. The working principle of the DSC is to heat a test sample and monitor the change of the thermal property of the sample. An abrupt change marks, the temperature of the Curie point.

There are also other methods adopted to determine the Curie temperature. Some of them determine the Curie temperature by the change of magnetism or the change of electricity resulted therefrom, as described for example, in Japanese Patent No. 61-51580, Soviet Union Patent No. 1318948, and French Patent No. 2486661. As compared to the DSC method, most of these methods require complicated and elaborate equipment to conduct the measurement.

The DSC method, although simple in equipment and easy to use, has the disadvantage that it is not applicable to materials exhibiting no significant abrupt change of heat absorbability around the Curie temperature. This is perhaps due to the low magnetic anisotropy energy and weak spontaneous magnetization of these materials. To overcome this difficulty, an external magnetic field may be applied to the test sample to increase the magnetic anisotropy energy and to straighten the spontaneous magnetization of the sample.

It is therefore an object of the invention to provide a method and the instrument thereof to measure the Curie point of materials by using an external magnetic field, especially the Curie point of ferromagnetic materials possessing low magnetic anisotropy energy and weak spontaneous magnetization, and thus exhibiting no abrupt change of thermal property when tested with a conventional thermal analyzer.

It is another object of the invention to provide a method and the instrument thereof which can provide a precise measurement of the Curie point and also measure the increment of the magnetic anisotropy energy.

It is a further object of the invention to provide a method and the instrument thereof which applies an external magnetic field to the test sample of a conventional DSC test, and by increasing the intensity of the magnetic field, the identification of the Curie point can be improved.

There is, therefore, provided a method and the instrument associated therewith for determining the Curie temperatures of ferromagnetic materials which display no significant abrupt change in heat absorption around the Curie temperatures thereof by means of a conventional thermal analyzer with externally added facilities to provide an external magnetic field. The abrupt change of heat absorption of ferromagnetic materials is significantly increased by adding an external magnetic field to increase the magnetic anisotropy energy thereof and to strengthen the spontaneous magnetization thereof.

Because the present method and the associated instrument increase the significance of the abrupt change of thermal property of a DSC sample material, in the resulting experimental data from the DSC test it is clearer and easier to identify the Curie temperature.

The following examples only are preferred embodiments of the instrument of the present invention and the experimental results thereof, and are compared with the results obtained with the conventional DSC test, described with reference to the accompanying drawings.

DETAILED DESCRIPTION OF THE INVENTION

Figure 1:
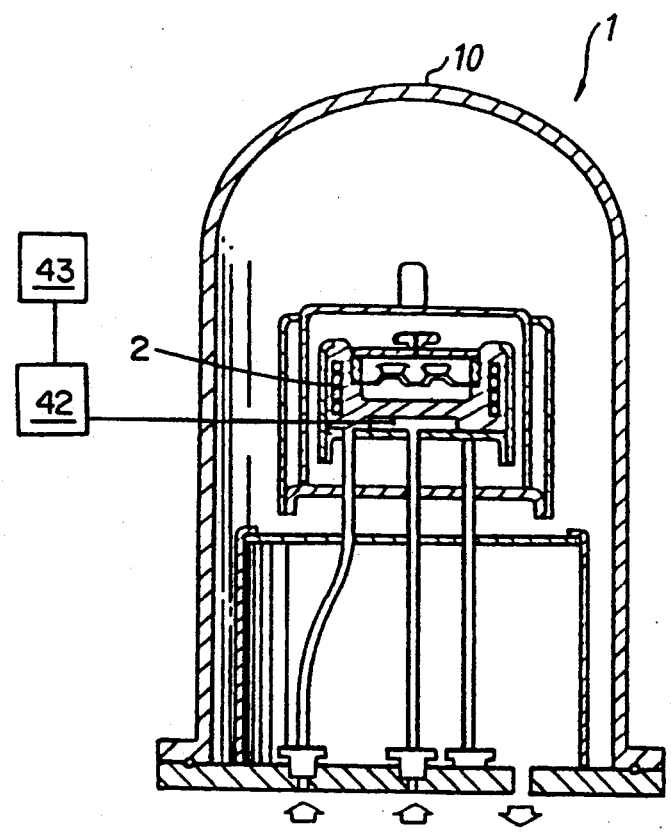
FIG. 1 shows a conventional thermal analyzer.
Figure 2:
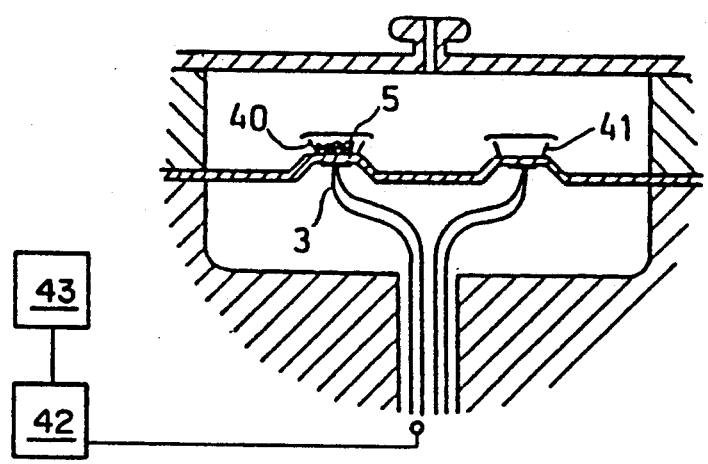
FIG. 2 shows a magnified view of a portion of the conventional thermal analyzer shown in FIG. 1.

With reference to FIGS. 1 and 2 which show a conventional thermal analyzer which is a commercially available DSC manufactured by Du Pont Co., U.S.A. (taken only as an example embodying the present invention). The basic elements of the DSC generally include a temperature detecting means or device 3 for detecting the temperature of test sample 5 while being heated by a heating device 2, the temperature detecting means sending signals comprising information of said detected temperature. An interpreting means 42 is provided for receiving the aforesaid signals sent by the temperature detecting means 3 for interpreting said signals, together with the thermal energy supplied by said heating device or means 2. The interpreting means provides results to a displaying and recording means 43 for displaying and recording the results that have been interpreted. A sample pan 40 is provided to support the test sample in place and a reference pan 41 is provided for comparison.

Figure 3:
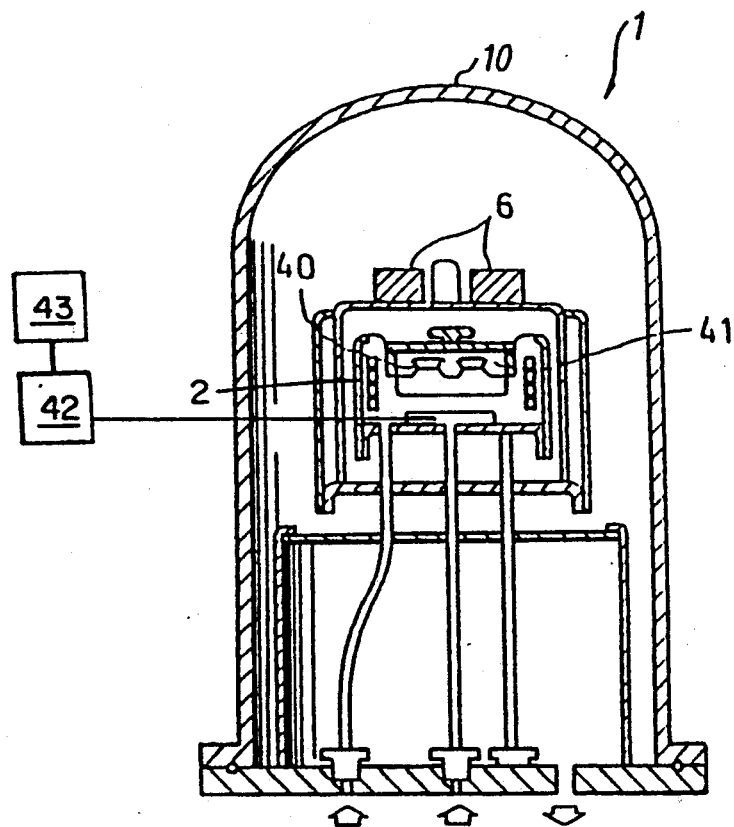
FIG. 3 shows an embodiment of the improvement over the conventional thermal analyzer of FIG. 1.
Figure 4:
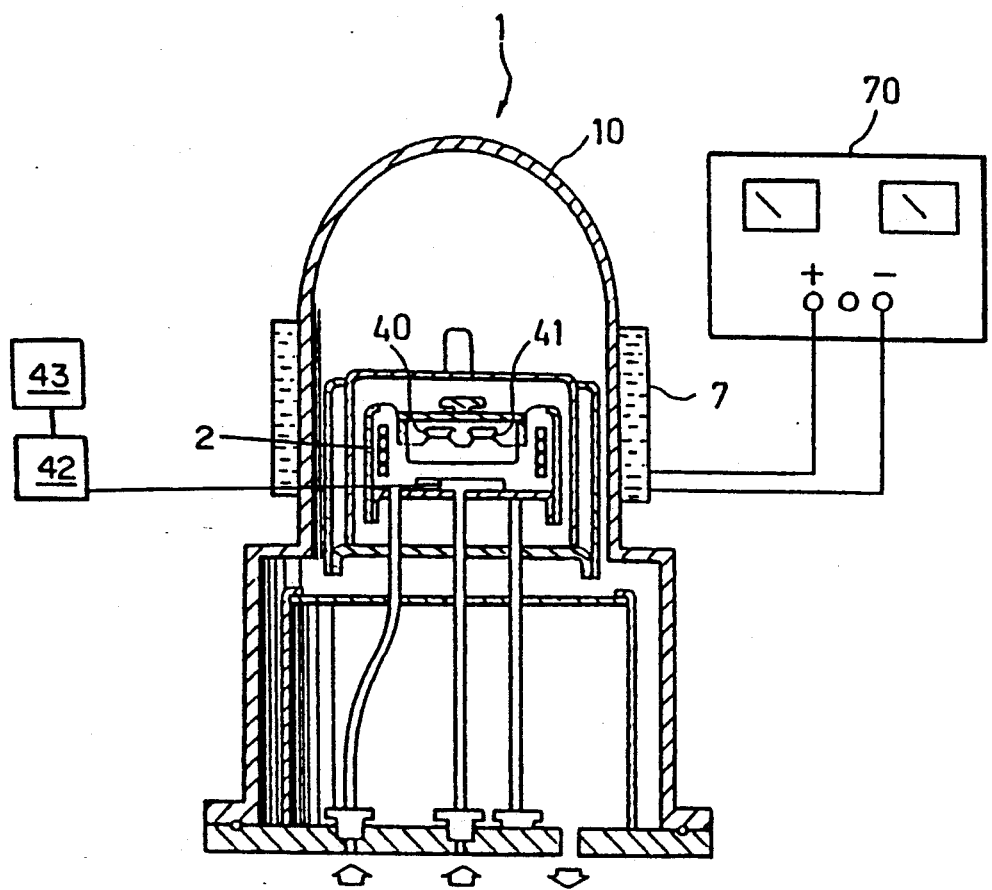
FIG. 4 shows another embodiment of the improvement over the conventional thermal analyzer of FIG. 1.
Figure 5:
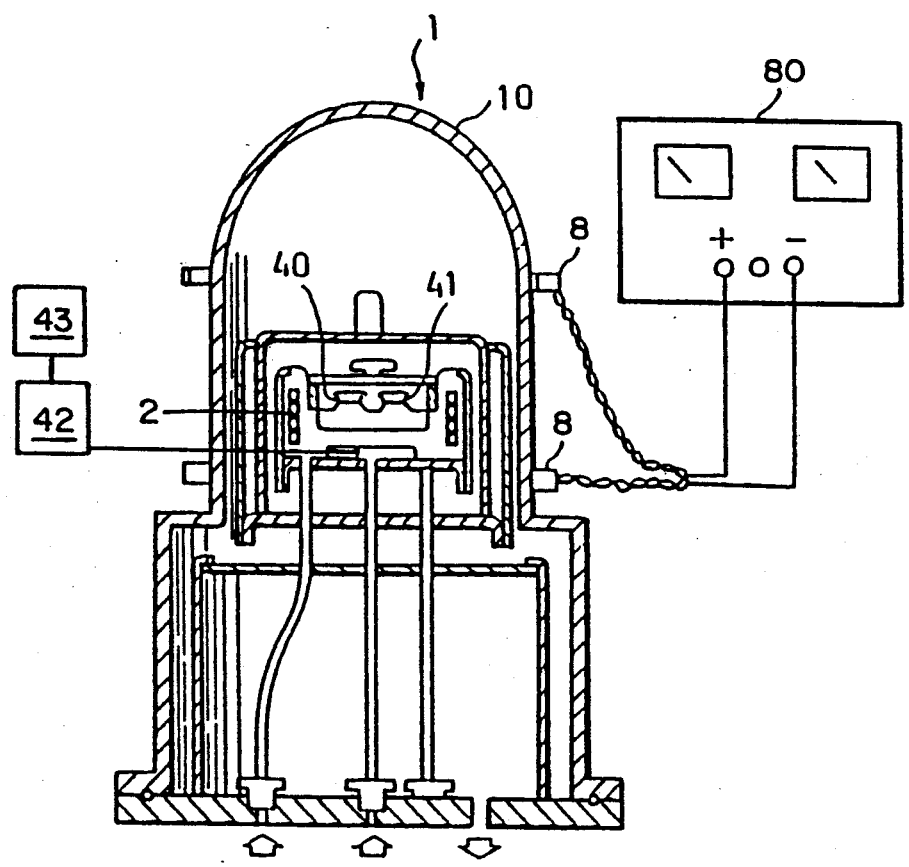
FIG. 5 shows a further embodiment of the improvement over the conventional thermal analyzer of FIG. 1.

Although the DSC described above is handy and convenient in determining Curie temperatures, it is not applicable to materials that have low magnetic anisotropy energy and weak spontaneous magnetization for the reasons set forth previously. To overcome this difficulty, an external magnetic field is necessary to strengthen the spontaneous magnetization of the sample when tested with a DSC. With reference to FIGS. 3, 4 and 5 wherein several different ways of adding an external magnetic field to a DSC are shown, in the first embodiment shown in FIG. 3, a permanent magnet 6 is disposed proximate to the test sample pan 40; in the second embodiment shown in FIG. 4, a solenoid 7 is wound around the DSC cell 1 and a power supply 70 is used to energized the solenoid 7; and in the third embodiment shown in FIG. 5, a Helmholtz coil 8 surrounds the DSC cell 1 to provide an external magnetic field when energized by a power supply 80.

Although only the DSC manufactured by Du Pont Co. is used to embody the invention and only three embodiments of the invention are exemplified herein, it is quite obvious that the same principle of increasing the magnetic anisotropy energy and strengthening the spontaneous magnetization with external magnetic fields is applicable to similar devices and a variety of similar embodiments can be carried out in both the above described DSC and other similar devices.

EXPERIMENT RESULT

Figure 6:
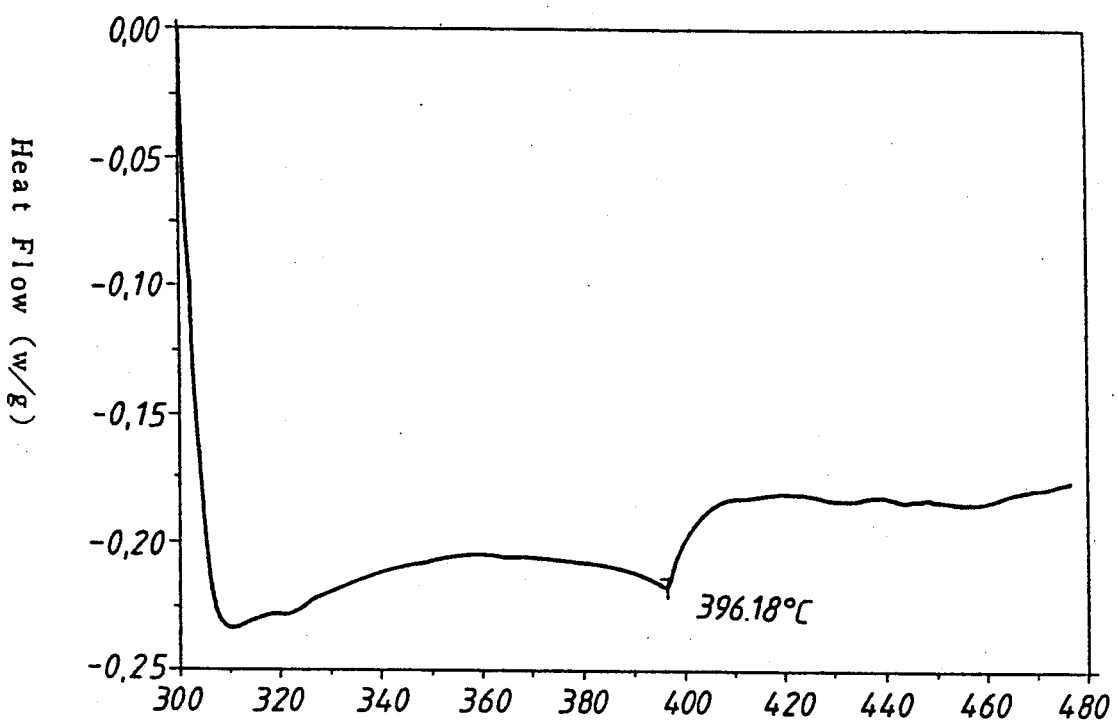
FIG. 6 is a plot of heat flow versus temperature showing clearly the Curie point when a $Fe_{78}Si_9B_{13}$ sample is tested in a conventional thermal analyzer of FIG. 1.
Figure 7:
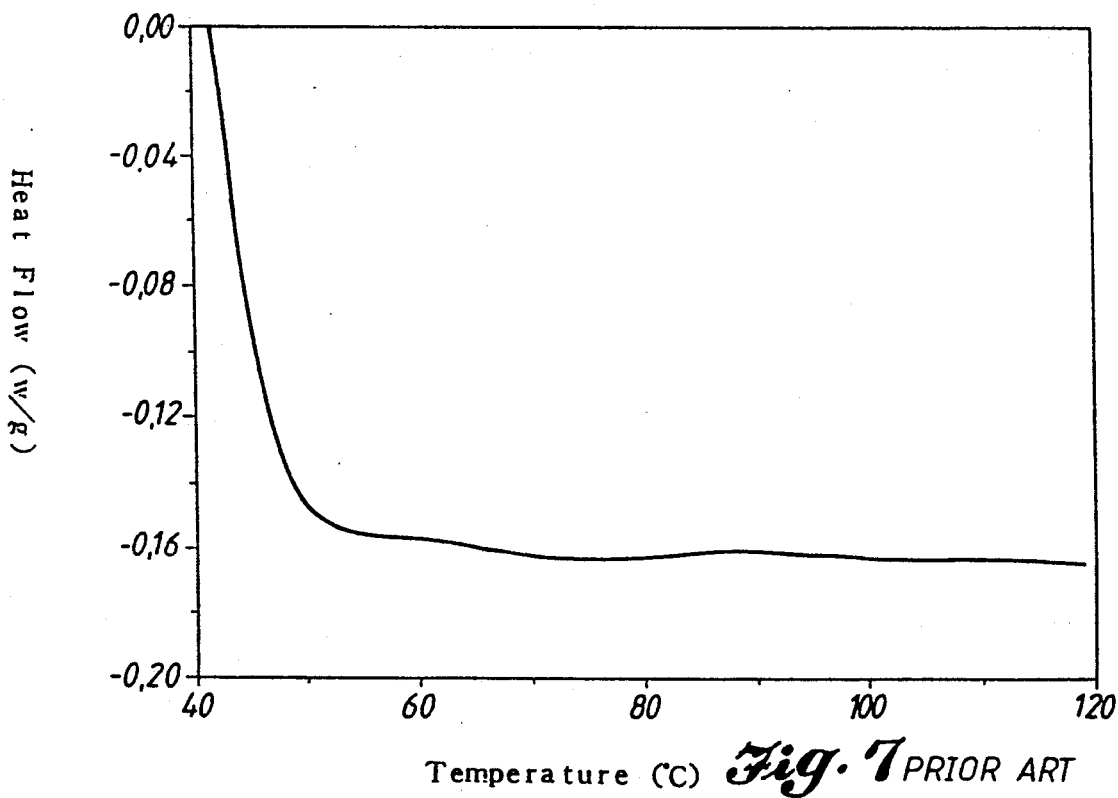
FIG. 7 is a plot of heat flow versus temperature with the Curie point very difficult or even impossible to identify when a $Fe_{90}Nb_{10})_{80}B_{20}$ sample is tested in a conventional thermal analyzer of FIG. 1.
Figure 8:
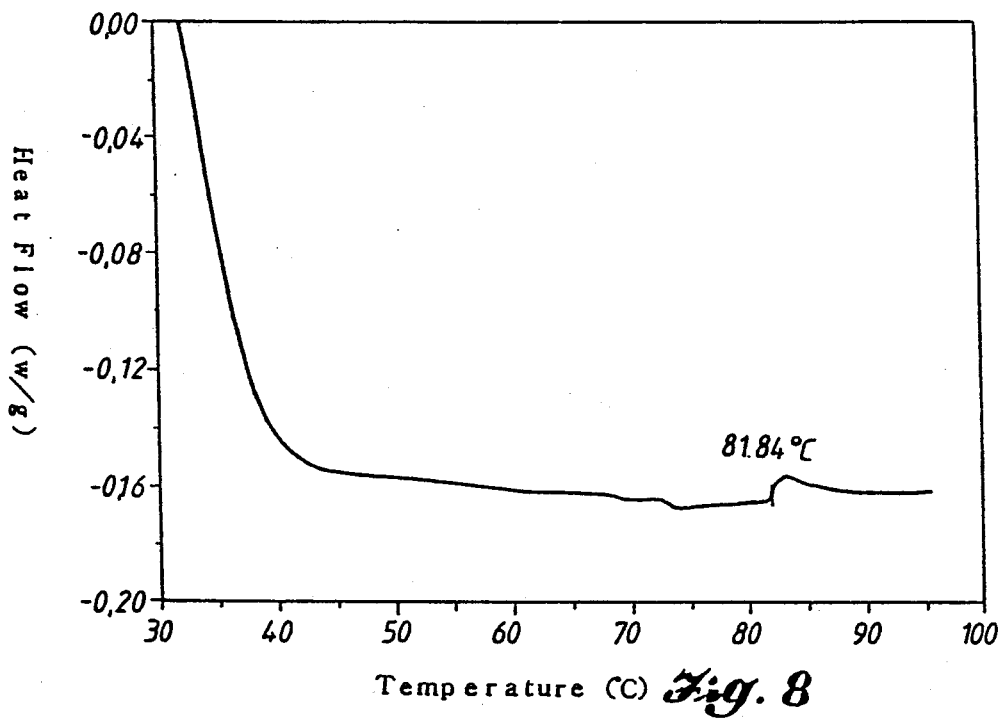
FIG. 8 is a plot of heat flow versus temperature of the same material tested in FIG. 7 obtained with the method in accordance with the present invention, wherein the Curie point is clearly identified.
Figure 11:
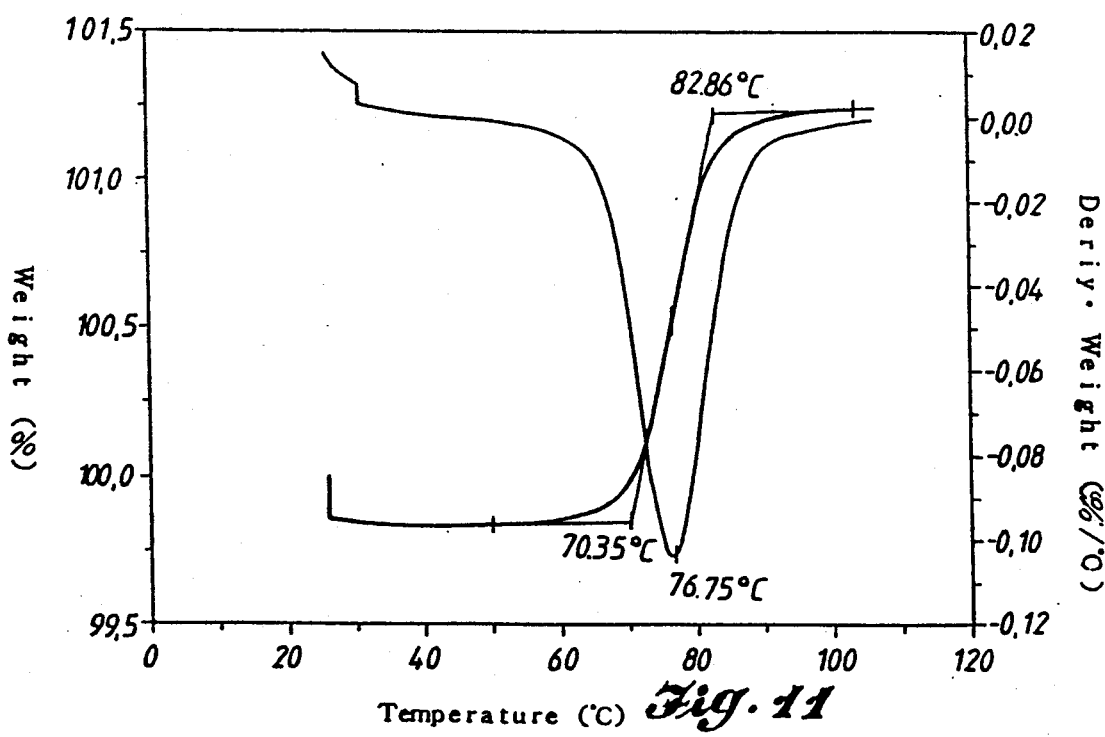
FIG. 11 is a TGA (thermal gravimetric analysis) plot of the material tested in FIG. 7 and 8 which shows that the Curie temperature is the same as detected by the method of the present invention, as that shown in FIG. 8.

In FIG. 6, a $Fe_{78}Si_9B_{13}$ sample, which is a ferromagnetic material showing abrupt change in heat absorption around its Curie temperature, is heated in a DSC described above. As can be observed from the drawing, the Curie temperature is clearly shown to be 396.18° C. This is a case which can be done with a conventional DSC, such as Du Pont's, while in FIG. 7, the test result of $(Fe_{90}Nb_{10})_{80}B_{20}$ with the same device shows no Curie point. However, by adding an external field to the device as shown in either FIGS. 3, 4 or 5, the Curie point of $(Fe_{90}Nb_{10})_{80}B_{20}$ can be clearly identified to be 81.84° C. This is shown in FIG. 8. This result is checked by the TGA test, as shown in FIG. 11.

Figure 9:
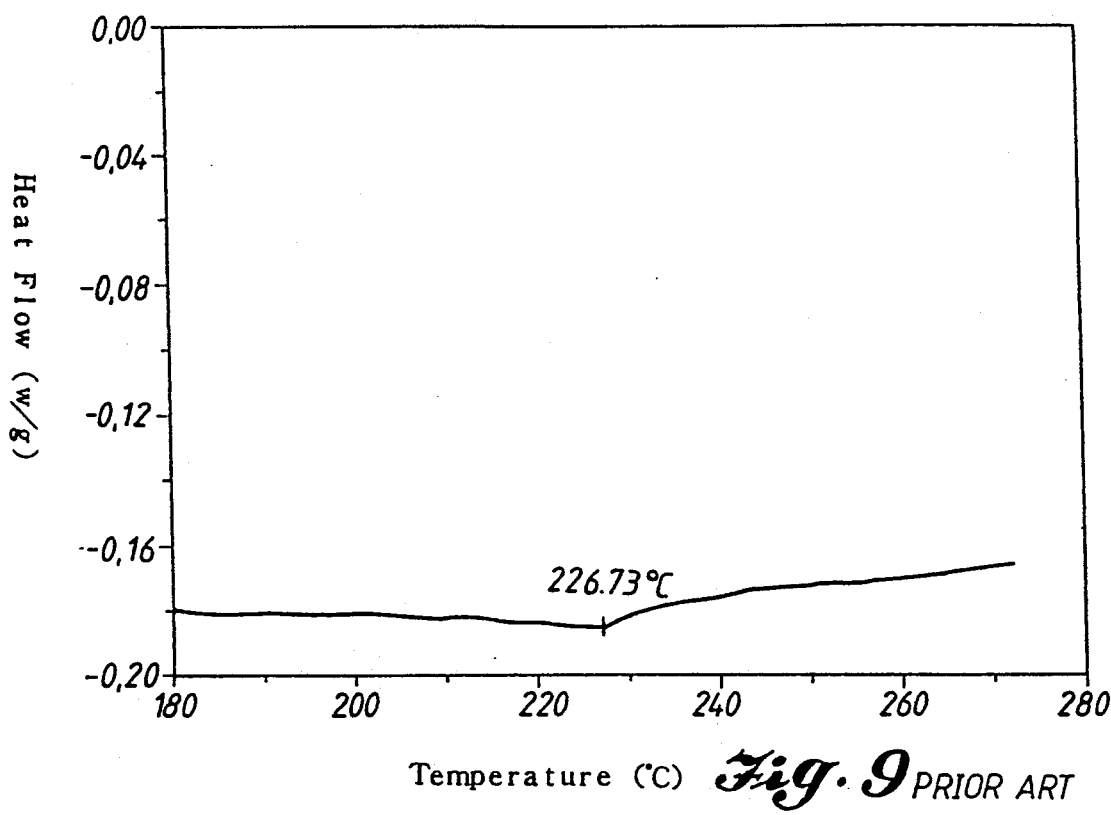
FIG. 9 is a plot of heat flow versus temperature of a $Co_{70}Fe_4Ni_2Si_{13}B_{11}$ sample obtained with a conventional thermal analyzer, wherein the Curie point is ambiguous.
Figure 10:
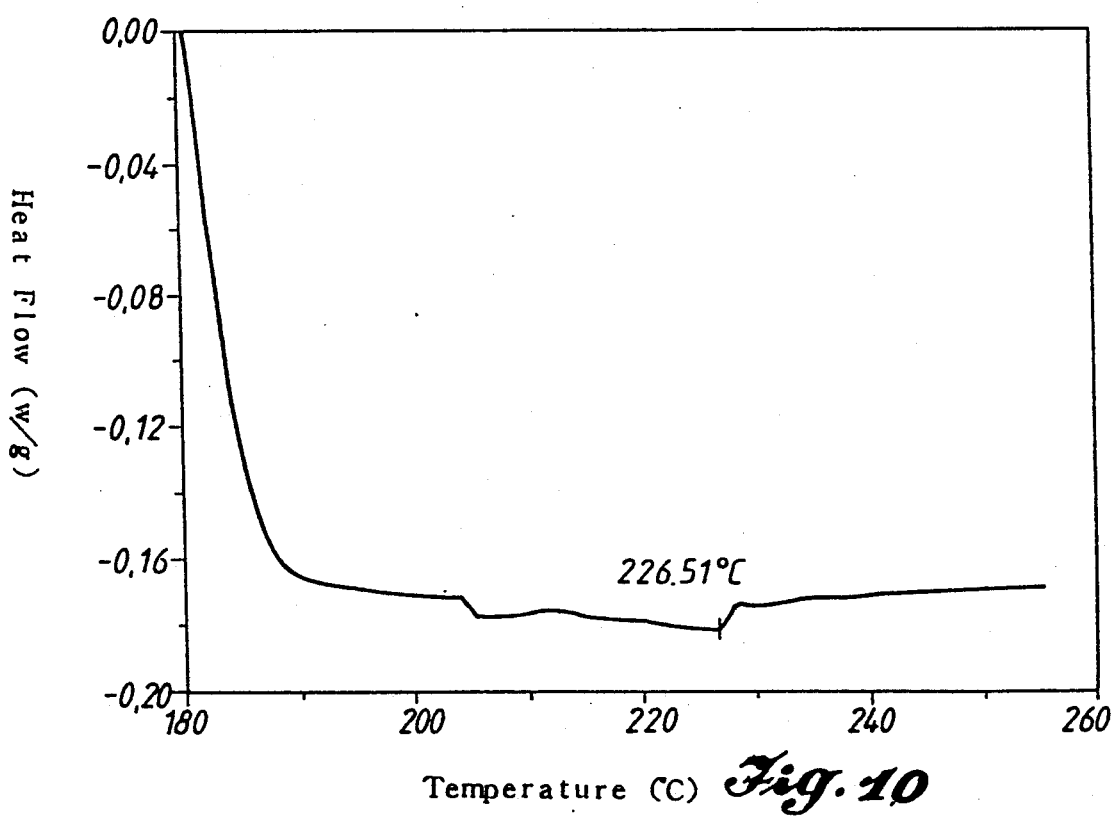
FIG. 10 is also a plot of heat flow versus temperature of a $Co_{70}Fe_4Ni_2Si_{13}B_{11}$ sample obtained with the method in accordance with the present invention, wherein the Curie point is more clearly identified.

FIG. 9 shows a test result of $Co_{70}Fe_4Ni_2Si_{13}B_{11}$ obtained with the conventional device shown in FIG. 1. The Curie point can be identified, but is ambiguous and not as clear as the case of FIG. 6. To more clearly identify the Curie point, an external magnetic field is applied to the test sample in accordance with the present invention. The result is shown in FIG. 10, and, as expected, the Curie point is more clearly identified.

With the above experimental result, it is clear that the invention is very helpful in determining the Curie temperatures of materials that have low magnetic anisotropy energy and weak spontaneous magnetization, and which thus show an ambiguous or even no Curie point with the test result of a conventional device, as the one shown in FIGS. 1 and 2.

It should be noted again that although the invention has been described in connection with the preferred embodiments and proven with experimental results, it is contemplated that those skilled in the art may make applications of the principle and changes to the preferred embodiments of the present invention, without departing from the spirit and scope of the present invention, as defined in the appended claims.

I claim:

1. A thermal analyzer for determining the Curie temperature cf a ferromagnetic material comprising:
    a heating means for providing thermal energy to and thus heating a test sample of said ferromagnetic material,
    a supporting means for supporting said test sample in place while being heated,
    a temperature detecting means for detecting the temperature of said test sample while being heated and sending signals comprising information of said detected temperature,
    an interpreting means for receiving said signals sent by said temperature detecting means and interpreting said signals, together with the thermal energy supplied by said heating means and for determining the Curie temperature of said material by detecting an increase in the heat taken in by said material,
    a displaying and recording means for displaying and recording results interpreted and provided by said interpreting means,
    characterized in that said thermal analyzer further comprises a magnetic field generating means which is disposed so that an external magnetic field is provided thereby through said test sample when said test sample is heated within said thermal analyser so as to provide an identifiable and clear Curie point of said ferromagnetic material with said temperature information.

2. A thermal analyzer as claimed in claim 1, wherein said magnetic field generating means is a permanent magnet.

3. A thermal analyzer as claimed in claim 1, wherein said magnetic field generating means is a solenoid energized with a power supply.

4. A thermal analyzer as claimed in claim 1, wherein said magnetic field generating means is a Helmholtz coil energized with a power supply.

5. A thermal analyzer as claimed in claim 1, wherein said thermal analyzer is a differential scanning calorimeter and wherein said heating means, said supporting means and said temperature detecting means constitute a cell which is further shielded with a jar and said magnetic field generating means is disposed so that an external magnetic field is provided thereby through said cell.

6. A thermal analyzer as claimed in claim 5, wherein said magnetic field generating means is a permanent magnet.

7. A thermal analyzer as claimed in claim 5, wherein said magnetic field generating means is a solenoid energized with a power supply.

8. A thermal analyzer as claimed in claim 5, wherein said magnetic field generating means is a Helmholtz coil energized with a power supply.

9. A thermal analyzer as claimed in claim 1 or 5, wherein said test sample is an amorphous ribbon of $Fe_{90}Nb_{10})_{80}B_{20}$.

10. A thermal analyzer as claimed in claim 1 or 5, wherein said test sample is an amorphous ribbon of $Co_{70}Fe_4Ni_2Si_{13}B_{11}$.

11. A method of determining the Curie temperature of a ferromagnetic material by means of a thermal analyzer with an external magnetic field comprising the following steps:

placing a test sample of said ferromagnetic material in a supporting means of said thermal analyzer, heating said test sample with a heating means, generating said external magnetic field through said test sample with a magnetic field generating means, detecting the temperature of said test sample with a temperature detecting means while heating said test sample, and sending out signals comprising information of said temperature, interpreting said signals with an interpreting means, determining the Curie temperature of said material by detecting an increase in the heat taken in by said material using said interpreting means, and displaying and recording said interpreted signals with a displaying and recording means.

12. A method as claimed in claim 11, wherein said thermal analyzer is a differential scanning calorimeter and wherein said heating means, said supporting and said temperature detecting means constitute a cell of said differential scanning analyzer with said magnetic field generating means being disposed so as to provide an external magnetic field through said cell.

13. A method as claimed in claim 11, wherein said magnetic field generating means is a permanent magnet.

14. A method as claimed in claim 11, wherein said magnetic field generating means is a solenoid energized with a power supply.

15. A method as claimed in claim 11, wherein said magnetic field generating means is a Helmholtz coil energized with a power supply.

16. A method as claimed in claim 12, wherein said magnetic field generating means is a permanent magnet.

17. A method as claimed in claim 12, wherein said magnetic field generating means is a solenoid energized with a power supply.

18. A method as claimed in claim 12, wherein said magnetic field generating means is a Helmholtz coil energized with a power supply.

19. A method as claimed in claim 11 or 12, wherein said test sample is an amorphous ribbon of $(Fe_{90}Nb_{10})_{80}B_{20}$.

20. A method as claimed in claim 11 or 12, wherein said test sample is an amorphous ribbon of $Co_{70}Fe_4Ni_2Si_{13}B_{11}$.

* * * * *